(12) United States Patent
Serrano

(10) Patent No.: US 9,526,754 B1
(45) Date of Patent: Dec. 27, 2016

(54) PLANT POLYPHENOLS EXTRACTION AND ACTIVATION THEREOF

(71) Applicant: Manuel Serrano, Redwood, CA (US)

(72) Inventor: Manuel Serrano, Redwood, CA (US)

( * ) Notice: Subject to any disclaimer, the term of this patent is extended or adjusted under 35 U.S.C. 154(b) by 404 days.

(21) Appl. No.: 14/090,045

(22) Filed: Nov. 26, 2013

Related U.S. Application Data

(60) Provisional application No. 61/730,009, filed on Nov. 26, 2012.

(51) Int. Cl.
| | |
|---|---|
| *A61K 36/82* | (2006.01) |
| *A61K 36/61* | (2006.01) |
| *A61K 36/185* | (2006.01) |
| *A01N 65/08* | (2009.01) |
| *A01N 65/28* | (2009.01) |
| *A01N 65/42* | (2009.01) |
| *A61K 36/886* | (2006.01) |

(52) U.S. Cl.
CPC .............. *A61K 36/82* (2013.01); *A01N 65/08* (2013.01); *A01N 65/28* (2013.01); *A01N 65/42* (2013.01); *A61K 36/185* (2013.01); *A61K 36/61* (2013.01); *A61K 36/886* (2013.01)

(58) Field of Classification Search
CPC ....... A61K 36/185; A61K 36/61; A61K 36/82
USPC ................................................ 424/729, 725
See application file for complete search history.

(56) References Cited

U.S. PATENT DOCUMENTS

| | | | | |
|---|---|---|---|---|
| 6,071,541 | A * | 6/2000 | Murad | A61K 8/22 424/616 |
| 6,746,695 | B1 * | 6/2004 | Martin | A61K 36/185 210/656 |
| 7,709,031 | B2 * | 5/2010 | Greenway | A61K 31/192 424/1.69 |
| 7,820,207 | B2 * | 10/2010 | Eidenberger | A23L 1/3002 424/725 |
| 8,334,000 | B2 * | 12/2012 | Greenway | A61K 31/192 424/1.69 |
| 2010/0158885 | A1 * | 6/2010 | Huang | A61K 36/185 424/94.2 |
| 2011/0064711 | A1 * | 3/2011 | Eidenberger | A23L 1/30 424/94.1 |
| 2012/0328593 | A1 * | 12/2012 | Huang | A61K 31/192 424/94.4 |
| 2012/0329736 | A1 * | 12/2012 | Huang | A61K 31/192 514/25 |

FOREIGN PATENT DOCUMENTS

| | | | |
|---|---|---|---|
| CN | 101817865 | * | 9/2010 |
| NL | 7603556 | * | 10/1977 |

* cited by examiner

Primary Examiner — Chris R Tate

(57) ABSTRACT

Combinations of dried plants can be prepared to form a herbal medicine, including reacting, in hydrogen peroxide, a combination of the extraction of pomegranate rinds (*Punica Granatum*), green tea extract (*Camellia Sinensis*), guava leaves, (*Psididum Guajava*) and jamun (*Sysygum Cuminni*). The herbal medicine can be used to treat and cure diarrhea, as antibacterial, anti-inflammatory and wound healing.

6 Claims, 2 Drawing Sheets

$H_2O_2 + 2Mn^{2+} \xrightarrow{\text{Enzyme}} H_2O + 2Mn^{3+}$
Fig. 1A
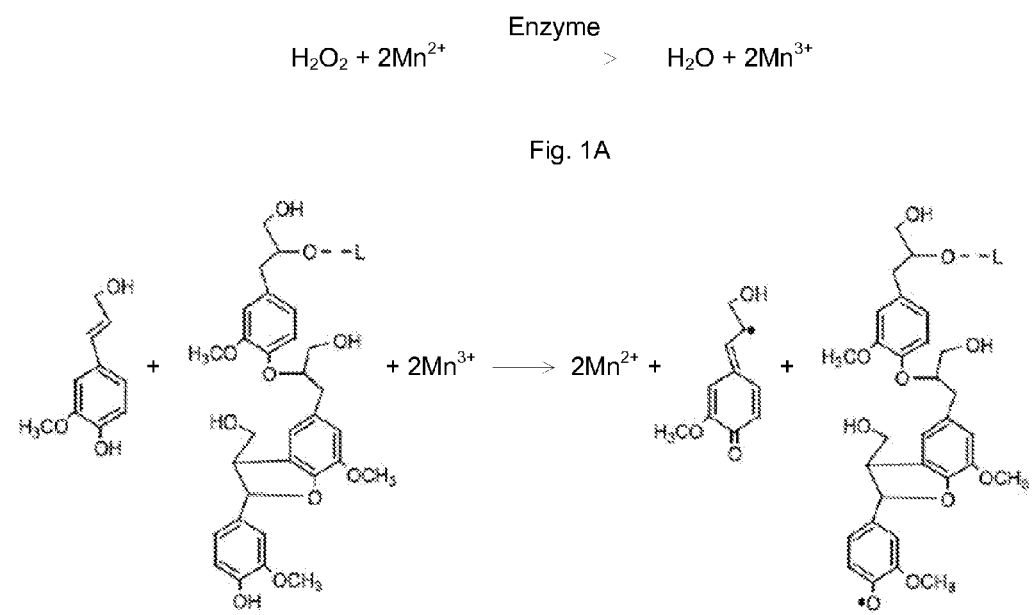
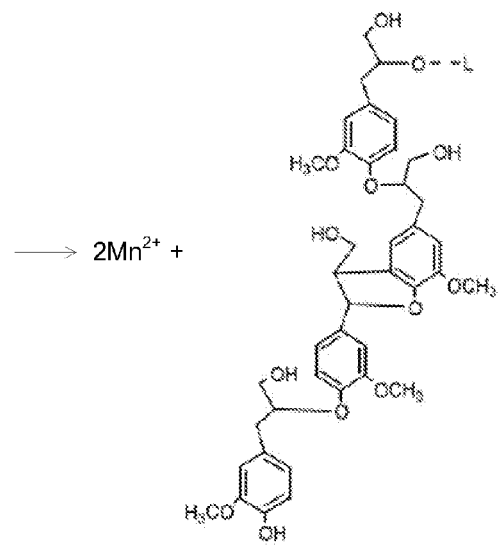
Fig. 1B

PLANT POLYPHENOLS EXTRACTION AND ACTIVATION THEREOF

This application claims priority of U.S. Provisional Application Ser. No. 61/730,009, filed on Nov. 26, 2012, entitled "Plant phenols extraction and activation thereof"; which is incorporated herein by reference.

The present invention relates to a method and process in the preparation of hydrogenated polyphenol particles. Particularly it relates to a process for preparing Polyphenols and second plant metabolites particles by a dispersing agent.

BACKGROUND

The uses of herbal medicines are known in cultures throughout the world. Herbal medicines are usually derived from plans or animals. Generally, there are minimal or no side effects in herbal medicines, perhaps because the active ingredients occur in nature, and often are combined to nullify the potential side effects of any one herb.

A characteristic of herbal medicines is that they can be slow acting, and thus are more suitable for maintaining good health than for treating an ailment.

SUMMARY

In some embodiments, processes are provided to selectively prepare and activate spherical polyphenol particles. By adding a dispersing agent, the polyphenol particles can include desired diameters without forming micelles. The methods can include extraction and the commercial production of spherical polyphenol particles.

In some embodiments, spherical polyphenol particles can be prepared by reacting phenols with hydrogen peroxide ($H_2O_2$) in a solution including water, an organic solvent compatible with water, a peroxidase and a dispersing agent. Polyphenols can be extracted, and spherical polyphenol particles can be prepared and activated by adding hydrogen peroxide into the solution to obtain a reaction mixture. The polymer emulsions of activated spherical polyphenol particles prepared according to some embodiments can be useful in the field of natural medicine, for example, having low viscocity, which can improve the efficiency of the medicine.

BRIEF DESCRIPTION OF THE DRAWINGS

FIGS. 1A-1B illustrate a reaction process for the preparation of the antibacterial solution according to some embodiments.

DETAILED DESCRIPTION

In some embodiments, formulations and combinations of plants are provided, which can be used to treat and cure diarrhea, as antibacterial, anti-inflammatory and wound healing. The plants can be commonly and traditionally used, and can be generally regarded as safe, for example, by the Food and Drug Administration (FDA) as generally recognized as safe (GRAS).

In some embodiments, the formulations can be prepared by combining the extraction of one or all of the following: pomegranate rinds (*Punica Granatum*) with green tea extract (*Camellia Sinensis*), guava leaves, (*Psididum Guajava*) and jamun (*Sysygum Cuminni*). The extraction can be performed in water and heated at 80° C. to 150° C., or at 80 to 110° C. Alternatively, the extraction can be performed in ethanol. Aloe vera juice or Hydrogen Peroxide can be added to the product or the aliquot obtained from the above extraction. The amount of added hydrogen peroxide can be between 1 and 7%, or can be between 0.001% and up to 3%. In some embodiments, the process forms an antibacterial component from the extraction of these materials. The antibacterial component can endogenously contain a secondary plant metabolite or tannin, a lignin, a flavonoid, a hydroxycoumarin, an alkaloid, or any combination thereof. The antibacterial component can be in dose ranging from 20 µg to 250 µg in the composition. In some embodiments, the chemicals, for example, hydrogen peroxide, are food grade.

Hydrogen peroxide can be use to cleanse at least a portion of the skin. For example, an amount of hydrogen peroxide can be included to cleanse the skin without substantial irritation. Aloe vera can act as a mild anesthetic, relieving itching, swelling, and pain. Aloe vera can also act as an antibacterial and antifungal agent, increases blood flow to wounded areas.

FIGS. 1A-1B illustrate a reaction process for the preparation of the antibacterial solution according to some embodiments. During the extraction of dried plant material compounds in water, hydro soluble tannin and polyphenols can be obtained, and then activated with hydrogen peroxide. The superoxide anion is a reduced form of molecular oxygen created by receiving one electron. In FIG. 1A, a peroxidase, e.g., $H_2O_2$ with enzyme as a catalyst, can oxidizes $Mn^{2+}$ to $Mn^{3+}$, which can diffuse through small pores in the cell wall. In FIG. 1B, monolignols and lignin can be present together in the cell wall. The $Mn^{3+}$ can then oxidizes monolignols and phenolic residues on the lignin polymer, forming monolignol radicals and phenolic radicals. The monolignol radical can couple with the phenolic radical on the lignin polymer. $Mn^{2+}$ can be released in the oxidation process, and the regenerated $Mn^{2+}$ can be ready for a new cycle.

Figure 2A:
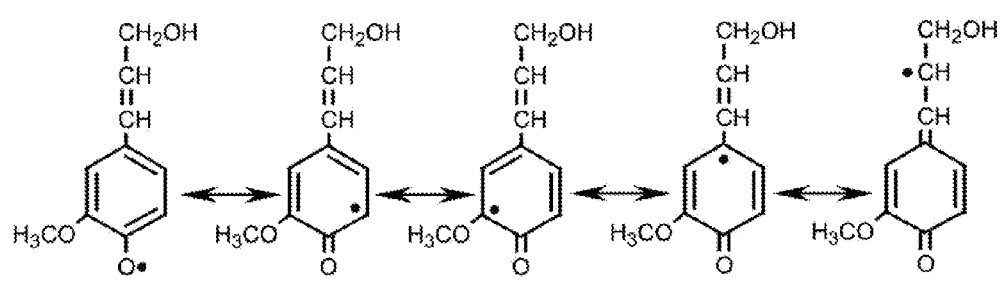
FIGS. 2A-2B illustrate different radicals on the monomer and polymer according to some embodiments.
Figure 2B:
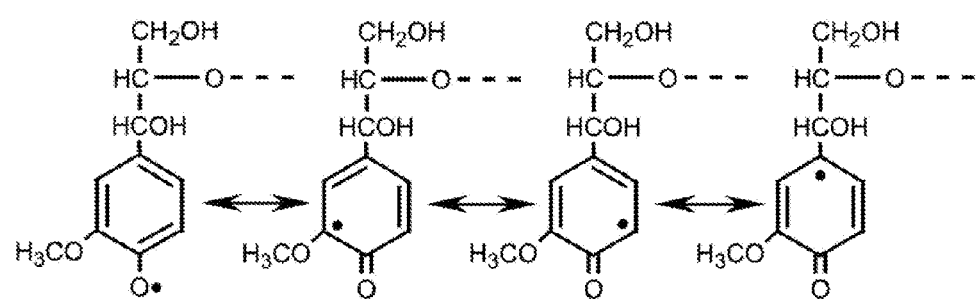

FIGS. 2A-2B illustrate different radicals on the monomer and polymer according to some embodiments. In FIG. 2A, radicals on the monomer are shown. In FIG. 2B, radicals on the polymer are shown.

In some embodiments, a kit including a dry form of the antibacterial composition is provided. The kit can allow ease of transportation and storage, and can quickly converted to an appropriate form for use.

In some embodiments, methods of treating bacteria-induced diarrhea, food poisoning, bacterial infection are provided, including orally administering to a subject an effective amount of the antibacterial composition. The methods can be used to treat bacteria infected water, including administering to the water an effective amount of the antibacterial composition. The methods can be used to treat or to prevent bacterial infection in a wounded tissue, or to treat bacteria infected tissue, including administering to the tissue an effective amount of the antibacterial composition.

In some embodiments, methods, and antibacterial compositions produced from the methods, are provided for producing an antibacterial composition. The methods can include combining pomegranate rinds (*Punica Granatum*) with green tea extract (*Camellia Sinensis*), guava leaves, (*Psididum Guajava*) and jamun (*Sysygum Cuminni*). The combination can be extracted in water and heated at 80° C. to 150° C. Alternatively, the combination can be extracted in ethanol solution. The combination can substantially denature enzymes endogenous. Aloe vera juice or Hydrogen Peroxide can be added to the product or the aliquot obtained from the above extraction. The amount of added hydrogen peroxide can be between 0.001 and up to 10 by vol %.

The extract can be performed by pressing the ingredients to provide a mash and then treating with a solvent to create an extract, then by filtering the extract to remove unwanted solids, and then separating the solvent from the filtered extract, for example by evaporating the solvent.

The composition can be in the form of dispersions, lotions, creams, gels, pastes, powders, aerosol sprays, syrups or ointments on sponges or cotton applicators, and solutions or suspensions in an aqueous liquid, non-aqueous liquid, oil-in-water emulsion, or water-in-oil liquid emulsion. The compositions can be applied topically. Other methods can be used, such as oral, rectal, parenteral, epicutaneous, transdermal, subcutaneous, intramuscular, intranasal, intradural, or intrarespiratory. In some embodiments, the composition can be applied to a sterile material, such as a gauze or a band aid.

In some embodiments, the composition can further include an antioxidant component to reduce the formation of free radicals, an oxidant, such as hydrogen peroxide, for the cleansing of skin to facilitate the prevention or treatment, and/or an moisturizing agent. The composition can further include a carrier.

Moisturizing agents can include any agent that facilitates hydration of the skin by inhibiting or preventing loss of water. For example, the moisturizing agents can minimize or prevent the skin from drying and cracking. The moisturizing agents can include hydrophobic agents, and hydrophilic agents, or any combinations thereof. The hydrophobic agents can include ceramide, borage oil (linoleic acid), tocopherol (Vitamin E), tocopherol linoleate, dimethicone, glycerine, and mixtures thereof. The hydrophilic agents can include hyaluronic acid, sodium peroxylinecarbolic acid (sodium PCA), wheat protein (e.g., laurdimonium hydroxypropyl hydrolyzed wheat protein), hair keratin amino acids, and mixtures thereof.

Antioxidant can include a vitamin C source, ascorbic acid, or a salt or ester thereof. Antioxidants can react with free radicals to neutralize the free radicals' effects, thus can minimize damage to cell membranes. Pomegranate extract and/or green tee extract can be used as antioxidant.

Other optional additives can also be used, such as a vitamin E source, a vitamin $B_3$ source, quercetin powder, pyridoxal 5 phosphate-Co $B_6$, and a vitamin A source.

In some embodiments, different plants and mixtures of plants can be used for preparing different herbal medicines. For example, for diarrhea, the following plants can be used, individually or in combinations: Amla, Barberry, Bilberry, Chamomile, Clove oil, Echinacea, Goldenseal, Gotu Kola, Meadowsweet, Noni, Red Raspberry, Skullcap. Slippery Elm, and St. John's Wort.

For digestive disorders, the following plants can be used, individually or in combinations: Astragalus, Bee Pollen, Burdock, Calendula, Cat's Claw, Cayenne Pepper, Fo Ti, Ginger, Goldenseal, Goldenseal, Green Tea, Holy Basil, Juniper, Kelp, Meadowsweet, Shilajit, and Turmeric.

For eczema, the following plants can be used, individually or in combinations: Aloe, Argan Oil, Bloodroot, Borage Seed Oil, Bupleurum, Burdock, Burdock, Calendula, Chamomile, Chickweed, Elder, Evening Primrose, Evening Primrose Oil, Flaxseed Oil, Fo Ti, Gotu Kola, Licorice, Milk Thistle, Pau D'arco.

For gastritis, the following plants can be used, individually or in combinations: Fennel Seed, Ginger, Goldenseal, Irish Moss, Lemon Balm, Marigold, Marshmallow, Peppermint, Shilajit, Slippery Elm. For dermatitis, the following plants can be used, individually or in combinations: Bloodroot, Borage Oil, Burdock, Cedarwood, Chickweed, Elder, Evening Primrose Oil, Peppermint, Sarsaparilla, St. John'S Wort, Tribulus, Yellow Dock.

For irritable bowel syndrome, the following plants can be used, individually or in combinations: Anise, Bupleurum, Chamomile, Evening Primrose Oil, Ginger, Hops, Lemon Balm, Peppermint, Psyllium, Slippery Elm, Wild Yam, Peptic Ulcers, the following plants can be used, individually or in combinations: Ashwagandha, Astragalus, Burdock, Cayenne, Chamomile, Chlorella, Dong Quai, Goldenseal, Licorice, Meadowsweet, Shilajit, Slippery Elm.

In some embodiments, the ratio of dried pomegranate rinds is between 0.3 to 0.6 wt % of water. The ratio of dried green tea extract is between 0.3 to 0.6 wt % of water. The ratio of dried guava leaves is between 0.05 to 0.2 wt % of water. The ratio of dried jamun is between 0.05 to 0.1 wt % of water. The total amount of dried plant materials can be between 0.005 wt % and 2 wt %, or can be between 0.3 and 2 wt % of water. The dried plant materials can be mixed in heated water, e.g., between room temperature and about 80° C. The mixture can be maintained for between 12 to 48 hours for dissolving of soluble materials. The liquid is filtered, and the insoluble materials are discarded. Food grade hydrogen peroxide can be added to the solution to make a solution mixture. The concentration of hydrogen peroxide that is used to add to the solution can be between 30 and 40 wt %. The concentration of hydrogen peroxide in the solution mixture can be between 0.05 and 3 vol %. The solution mixture is allowed to react for between 0.5 to 2 hour to promote cross linking of proteins into aggregates. Some additional hydrogen peroxide (about 0.01 to 0.1 vol %) can be added to the solution mixture saturate available binding sites in the solution mixture. The solution is then allowed to react for at least 2 hours, such as between 8 and 24 hours. The solution is then dilute with water to reduce the hydrogen peroxide concentration to between 0.01 to 0.04 vol %. The diluted solution is left at room temperature for between 2 to 10 days to allow unbound hydrogen peroxide to degrade. The solution is then diluted to desired concentration for packaging.

As an example, 5 grams of dried pomegranate rinds, 4 grams of dried green tea extract, 1 gram of dried guava leave, and 1 gram of dried jamun are mixed in a liter of water. The pulverized plant materials are mixed at room temperature, and left at room temperature for about 24 hours. The liquid is then passed through a 5 micron filter. 35% vol food grade hydrogen peroxide is added to the plant-water solution to make a solution mixture having 1 vol % concentrated hydrogen peroxide. The solution mixture is left for 10 hour. The solution is then dilute with water to reduce the hydrogen peroxide concentration to 0.001% up to 3 vol %. The diluted solution is left at room temperature for a few days before packaging.

What is claimed is:
1. A method for preparing an herbal medicine for use in treating a skin wound, the method comprising:
  extracting, in water, effective amounts of pomegranate rind, green tea, guava leaves and jamun—in combination, while mixing the combination in the water for a period of between 12 and 48 hours to obtain an aqueous extract;
  filtering the aqueous extract to obtain a filtered aqueous extract;
  adding hydrogen peroxide to the filtered aqueous extract at a concentration of between 0.05 vol % and 3 vol % to obtain a solution mixture, and letting the solution mixture stand for a period of between 0.5 and 24 hours; and diluting the solution mixture with water to reduce the hydrogen peroxide in the solution mixture to a concentration of between 0.01 to 0.04 vol % to obtain said herbal medicine.

2. The method according to claim 1, wherein the ratio of the pomegranate rind, green tea, guava leaves, and jamun is about 5:4:1:1, respectively.

3. A method for preparing an herbal medicine for use in treating a skin wound, the method comprising:

extracting, in water, effective amounts of pomegranate rind, green tea, guava leaves and jamun—in combination, while mixing the combination in the water for a period of between 12 and 48 hours to obtain an aqueous extract;

filtering the aqueous extract to obtain a filtered aqueous extract;

adding hydrogen peroxide to the filtered aqueous extract at a concentration of between 0.05 vol % and 3 vol % to obtain a first solution mixture, and letting the first solution mixture stand for a period of between 0.5 and 24 hours;

diluting the first solution mixture with water to reduce the hydrogen peroxide to a concentration of between 0.01 to 0.1 vol % to obtain a second solution mixture, then letting the second solution mixture stand for a period of between 2 and 10 days; and diluting the second solution mixture with an additional amount of water to obtain said herbal medicine.

4. The method according to claim 3, wherein the ratio of the pomegranate rind, green tea, guava leaves, and jamun in the combination is about 5:4:1:1, respectively.

5. A method for preparing an herbal medicine for use in treating a skin wound, the method comprising:

extracting, in water, effective amounts of pomegranate rind, green tea, guava leaves and jamun—in combination, while mixing the combination in the water for a period of between 12 and 48 hours to obtain an aqueous extract;

filtering the aqueous extract to obtain a filtered aqueous extract;

adding hydrogen peroxide to the filtered aqueous extract at a concentration of between 0.05 vol % and 3 vol % to obtain a first solution mixture, then letting the first solution mixture stand for a period of between 0.5 to 2 hours;

adding an additional amount of hydrogen peroxide to the first solution mixture, wherein the concentration of additional hydrogen peroxide is between about 0.01 to 0.1 vol %, to obtain a second solution mixture, then letting the second solution mixture stand for a period of between 2 and 24 hours;

diluting the second solution mixture with water to reduce the hydrogen peroxide in the second solution to a concentration of between 0.01 to 0.04 vol % to obtain said herbal medicine.

6. The method according to claim 5, wherein the ratio of the pomegranate rind, green tea, guava leaves, and jamun in the combination is about 5:4:1:1, respectively.

* * * * *